United States Patent [19]

Lenormand et al.

[11] Patent Number: 5,253,529
[45] Date of Patent: Oct. 19, 1993

[54] MEASUREMENT OF CONSTITUENTS OF A CENTRIFUGED SYSTEM BY EMISSION/RECEPTION OF MECHANICAL SIGNALS

[75] Inventors: Roland Lenormand; Pierre Forbes, both of Rueil Malmaison; Moricio Hoyos, Epinay sur Seine; Francoise Deflandre, Argenteuil, all of France

[73] Assignee: Institut Francais du Petrole, Rueil Malmaison, France

[21] Appl. No.: 749,774

[22] Filed: Aug. 26, 1991

[30] Foreign Application Priority Data

Aug. 27, 1990 [FR] France .................. 90 10755

[51] Int. Cl.⁵ ............................. G01N 29/00
[52] U.S. Cl. ........................ 73/597; 422/72; 436/45; 494/10; 73/61.45
[58] Field of Search .......... 73/61.4, 597, 61.1 R, 73/61.69, 61.72, 61.75, 61.79, 594, 61.45; 422/72; 436/45; 494/10, 16

[56] References Cited

U.S. PATENT DOCUMENTS 4,671,102 6/1987 Vinegar et al. ............... 73/61.1 R

FOREIGN PATENT DOCUMENTS 2556836 6/1985 France .
632941 11/1978 U.S.S.R. ..................... 73/61.4

Primary Examiner—Hezron E. Williams
Assistant Examiner—Nashmiya Ashraf
Attorney, Agent, or Firm—Millen, White, Zelano & Branigan

[57] ABSTRACT

In a process and apparatus for measuring the distribution of the concentrations of constituents of a centrifuged medium containing at least one fluid, during centrifuging, a mechanical signal, preferably a sound wave, is emitted from at least one emission point (19-22) in contact with or in the immediate vicinity of the medium (16). The emitted signal is received by at least one reception point (20-22) in contact with or in the immediate vicinity of the medium. For each emission-reception point pair, at least one propagation characteristic of the signal between the emission and reception points thereof is measured and, by an appropriate processor (15), the distribution of the concentrations of the constituents present in the medium is determined. A proposed application is the calculation of the relative permeability and capillary pressure curves of fluids in a porous medium in order to improve the working and operation of oil fields.

18 Claims, 6 Drawing Sheets

MEASUREMENT OF CONSTITUENTS OF A CENTRIFUGED SYSTEM BY EMISSION/RECEPTION OF MECHANICAL SIGNALS

BACKGROUND OF THE INVENTION

The present invention relates to a process for measuring the distribution of the concentrations of constituents of a centrifuged medium, an apparatus for performing the process and the use of the apparatus.

For controlling the operation of an oil field, the petroleum industry makes use of numerical simulations in order to forecast the impact of a given operating method on the field. This forecast requires the characterization of the properties of the outflows in the field, including the evolution of the capillary pressure and the relative permeabilities of the fluids present.

These latter properties are primary focus in evaluating workable reserves or the productivity of a field, and, over several decades, different measuring means for these properties on samples have been proposed.

One of the most widely used methods is centrifuging due to its speed, ease of performance and its possible automation (J. Hagoort, 1980: "Oil Recovery by Gravity Drainage, SPE Journal", 1980, pp. 139–150; Hassler and Brunner, "Measurements of Capillary Pressure in Small Core Samples, Trans. AIME", 160, 1945, pp. 114–123).

Centrifuging can be used according to French Patent 2,556,836 for fractional separation and grain size analysis of particles suspended in a liquid, coupled with an ultrasonic thickness sensor located outside the rotor facing the centrifugal chamber.

However, generally, centrifuging only makes it possible to measure the mean saturation of the fluids in the centrifuged sample. Therefore, it is an indirect method for obtaining the capillary pressure Pc and relative permeabilities as a function of local saturations S.

The capillary pressure Pc(S) is obtained from measuring the mean saturation, under steady state conditions, at different centrifuging speeds, averaging out certain calculation approximations and certain hypotheses on the exact distribution of the fluids and the flow conditions in the sample (limit conditions, end effects, sample homogeneity, uniform displacement, etc.). The approximations and calculation methods have been progressively improved and would now appear to be satisfactory. However, the hypotheses concerning the local distribution of the fluids and flow conditions are contradictory.

The relative permeabilities kr(S) are obtained on the basis of the evolution, under non-steady state conditions, of the mean saturation and the Pc(S) on the basis of an explicit calculation or in accordance with an implicit adjustment by a numerical model simulating centrifuging known in the art.

It would appear that these relative permeabilities are highly dependent on the function Pc(S). Moreover, these very different relative permeabilities can lead to comparable evolutions of the mean saturation in a centrifuged sample, although the local distribution of the saturation evolves in a very different way.

Both for the calculation of Pc(S) and for that of kr(S), it would appear that the measurement of the mean saturation during centrifuging is not sufficiently discriminating enough.

The measurement of local saturations in the sample would appear to be a means for obtaining a direct measurement of Pc(S), a discriminating calculation of kr(S) and a verification of standard hypotheses concerning the exact distribution of the fluids in the sample.

Aiming at this improvement, Vinegar et al, (U.S. Pat. No. 4,671,102) provide means for measuring the local distribution of saturations in a centrifuged sample. Said means consists of using one or more electromagnetic sources (X-ray or other radiation) irradiate the sample, followed by analysis of the transmitted radiations. Such means would be quite suitable for determining the distribution of local saturations and variation in time during centrifuging. However, implementation of this procedure has encountered as yet unsolved technical problems, possibly be due to the overall dimensions of the source or to the dangers inherent in handling X-ray or other sources of radiation, or in the absorption of radiation by the numerous metal parts normally present in a centrifuge.

SUMMARY OF THE INVENTION

Therefore, the present invention provides a novel and improved method and means for measuring the distribution of the saturations of fluids in a centrifuged porous medium which is easier to perform, much less expensive and leads to good results. Use is made of the emissions of mechanical signals which are transmitted through most metals. Thus, said means allows for measurement on media under high pressures and temperatures (such as those which exits in an oil field) which normally require the use of metal enclosures, thereby rendering prior art methods ineffective.

In addition, said means can be applied in more general terms to measuring the concentrations of constituents of a centrifuged system, such as the concentrations of particles in a suspension or the fluid concentrations, e.g., in an emulsion.

More specifically, the present invention relates to a process for the measurement of the distribution of the concentrations of constituents of a medium containing at least one fluid, comprising centrifuging under appropriate conditions of the medium in a centrifuge and characterized by the following stages:

a) during centrifuging, a mechanical signal is emitted in an adequate frequency and intensity range from at least one emission point in contact with or in the immediate vicinity of the centrifuged medium;

b) the corresponding transmitted signal is received by at least one reception point in contact with or in the immediate vicinity of the centrifuged medium after the mechanical signal has traversed at least a part of the said medium;

c) for each pair of emission and reception points, a measurement is performed of at least one propagation characteristic of the mechanical signal, such as the propagation velocity in the medium between the emission point and the reception point of said signal; and d) the distribution of the concentrations of the constituents in the medium is determined by appropriate processing means from said measurements of the propagation characteristics of the signal.

The process of the invention is advantageous in that it can be performed simply and quickly; it is inexpensive, requiring no doping or modification of the constituents to be measured; it does not require dangerous sources of radiation and is possible to operate through a large number of materials which are often opaque to radiation and X-ray, in particular. Thus, it permits the measurement of media under high temperature or pressure conditions requiring the use of metal enclosures.

The studied medium is preferably a porous medium containing two fluids. According to a feature of the invention, a plurality of emitters can simultaneously or successively emit a mechanical signal at a plurality of points on the medium or in its immediate vicinity.

According to another feature, during stage b, at least one emission point can be used at least once as the reception point.

According to another feature of the process, it is possible to repeat at different times the aforementioned stages a, b, c and d to obtain the distribution of the constituents of the medium at predetermined times, e.g., corresponding to different stages of the centrifuging process.

According to another feature of the process, a plurality of emission points and a plurality of reception points can be placed in the plane of a section of the centrifuged medium. Then, in accordance with the inventive process, the distribution of the concentrations of the constituents of the medium in plane are determined to obtain a two-dimensional image of the distribution of said constituents in said plane.

Finally, according to another feature of the invention, it is possible to have a plurality of emission points and a plurality of reception points along a given direction, preferably that of the centrifuge arm. The mean concentrations of the constituents in this direction are then determined, so that a concentration profile is obtained (dimension 1).

The invention also relates to an apparatus for measuring the distribution of the concentrations of constituents of a medium, the apparatus comprising in combination:

a centrifuge capable of operating at a plurality of rotation speeds and having a predetermined number of sample holders containing a given medium, said sample holders being able to receive a plurality of emitters and receivers, the centrifuge also having suitable rotary contact means for transmitting, during rotation, electrical signals used for producing the mechanical signals emitted and for measuring the signals received;

at least one emission source for the mechanical signals located in the immediate vicinity of the sample holder and capable of supplying an adequate range of frequencies and intensities;

at least one reception means for transmitted signals which have traversed the medium, located in the immediate vicinity of the sample holder;

means for measuring the propagation characteristics of the mechanical signals, linked with the emission sources and the reception means via the adapted rotary contact means; and processing and checking means connected to said measuring means and to said centrifuge for measuring the distribution of the concentrations.

The invention is advantageously applied to the measurement of the saturation of two fluids in a centrifuged porous medium. The measurements obtained can then be used with greater precision for calculating the capillary pressure and relative permeabilities as a function of local saturation.

The centrifuge used can be a conventional automated centrifuge able to rotate the porous medium at a variety of constant and/or irregular rotation speeds, preferably between 500 and 10,000 r.p.m.

The porous medium is generally placed, e.g., metallic sample holder buckets or cups. The latter can optionally have a ferrule for collecting and measuring fluid leaving the medium during centrifuging. An alternating illumination, synchronized with the rotation (stroboscopy), can be used for this measurement.

One or more mechanical signal generators are generally placed in the immediate vicinity of or within the sample holder, i.e., on the periphery of or in contact with the porous medium, on the periphery of or within the cup containing it, or between the medium and the cup (FIG. 1). These generators can, e.g., be sound transducers, optionally produced from piezoelectric ceramics, capable of supplying mechanical signals with frequencies generally between 100 and 2000 kHz.

The mechanical signals emitted can be sufficiently intense and brief to traverse the centrifuged medium in a sufficiently short time to ensure that the displacement of the fluids within the medium is very short during this time. The intensity of the emitted signal is chosen in such a way that the signal received is accessible to the detector. It is a function of the traversed porous medium. This also applies with respect to the wavelength or wavelengths of the emission signal.

Preferably, these signals are sound waves with frequencies between 100 and 2,000 kHz and advantageously between 250 and 500 kHz which are generated by voltages (FIG. 1) generated, checked or amplified by a function generator. Typically, use is made of a monofrequency wave in the same ranges.

One or more mechanical signal generators can be activated simultaneously or successively. In the case of successive emissions, called emission series, the succession can be sufficiently brief to enable a very small displacement of the fluids in the interior, so as to obtain quasi-simultaneous emissions compared with the evolution speeds of the fluids in the medium.

The mechanical signals can be received by one or more receivers, which can optionally be the emitters, generally placed in the immediate vicinity of or within the sample holder, i.e., on the periphery or in contact with the porous medium, on the periphery or within the cup containing it, between the medium and the cup, or on or in the support carrying the cup. The signals received can be transformed into optionally amplified electric signals. The mechanical signals received are compared with the emitted signals, e.g., a comparison between the electric emission and reception signals.

For each emission or emission series, characteristics of the propagation of the mechanical signals between each emitter-receiver pair can, be deduced from said comparison. These characteristics can e.g., be the propagation velocity of the signals, their displacement time or their attenuation (FIG. 1).

For each emission or emission series, a mean value of these characteristics is obtained for each emitter-receiver type. In the case of emission series, a tomography-type method can be used for reconstructing a two or three-dimensional image of the local values of these characteristics.

A calibration method, an example of which is given below, makes it possible to transfer each of these values into a value of the concentration of the constituents of the system.

As a function of the number and position of the emitter-receiver pairs, a profile (FIG. 1), a two-dimensional projection or a three-dimensional distribution of the concentrations is obtained. The calculation method can use a computer coupled to the equipment and an example of this method is described below.

The complete procedure can be repeated at different times in a periodic or non-periodic manner. Thus, for different instants, a profile, a 2-dimensional projection or a 3-dimensional distribution of the concentrations are obtained. One calculation method can be then used for obtaining the variations in time of said profile, two-dimensional projection or three-dimensional distribution of the concentrations, as well as the variations in time of the concentrations at one or more locations of the centrifuged medium.

The complete method can be performed for systems under a controlled temperature T and confinement pressure P. For example, the distributions and concentrations of the constituents can be obtained under the T,P conditions of oil tanks.

BRIEF DESCRIPTION OF THE DRAWINGS

The invention is described in greater detail hereinafter relative to non-limitative embodiments of the process and apparatus according to the invention and the attached drawings, wherein show.

DETAILED DESCRIPTION OF THE DRAWINGS

Figure 1:
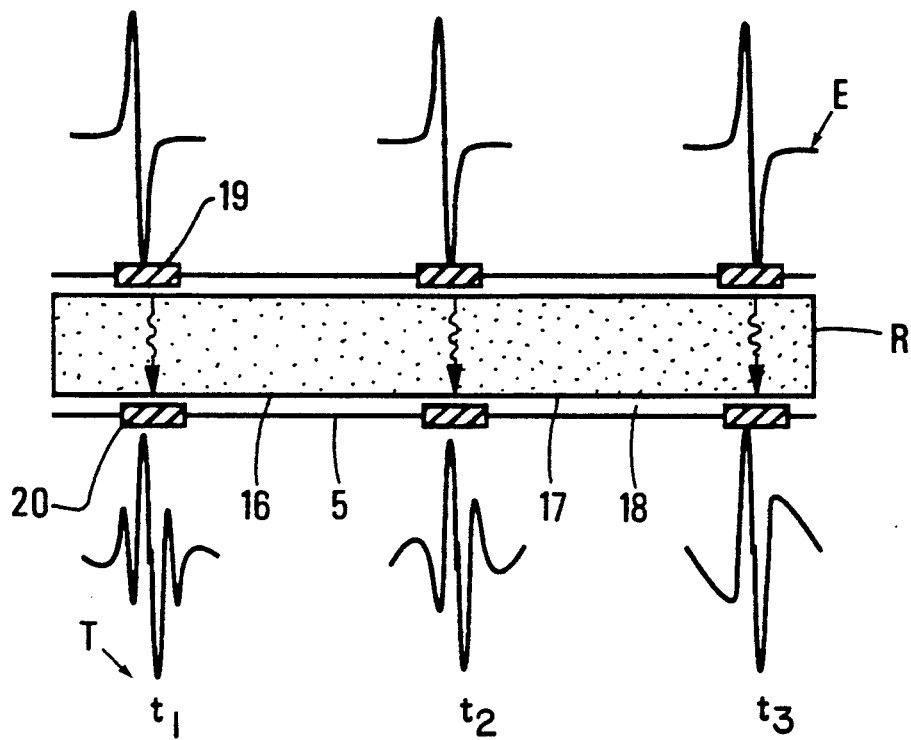
FIGS. 1 and 1A illustrate the general principle of the use of mechanical signals for measuring the saturations of fluids in a centrifuged porous medium and the determination of saturation profiles along the porous medium.
Figure 1A:
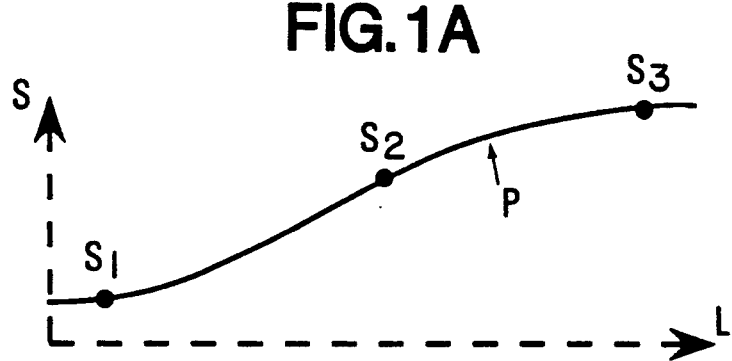

FIG. 1 shows an example of the application of the method. An electric signal (E) is transmitted to one or more mechanical signal generators (19) e.g. positioned along a porous medium (16) containing two centrifuged fluids in a sample holder (5). The generators transform the electric signal e.g. into a sound wave (A), which traverses a part of the medium before being received by one or more receivers (20). The receivers transform the signals received into electric signals (R) which, compared with the emitted signal (E), supply one of the propagation characteristics in each traversed part of the porous medium, e.g. the time of flight (t). This characteristic then makes it possible to calculate the saturation (S) of the fluids in each of these parts and to constitute distribution images of this saturation e.g. in the form of profiles (P) along the extension (L) of the porous medium (FIG. 1A).

Figure 2:
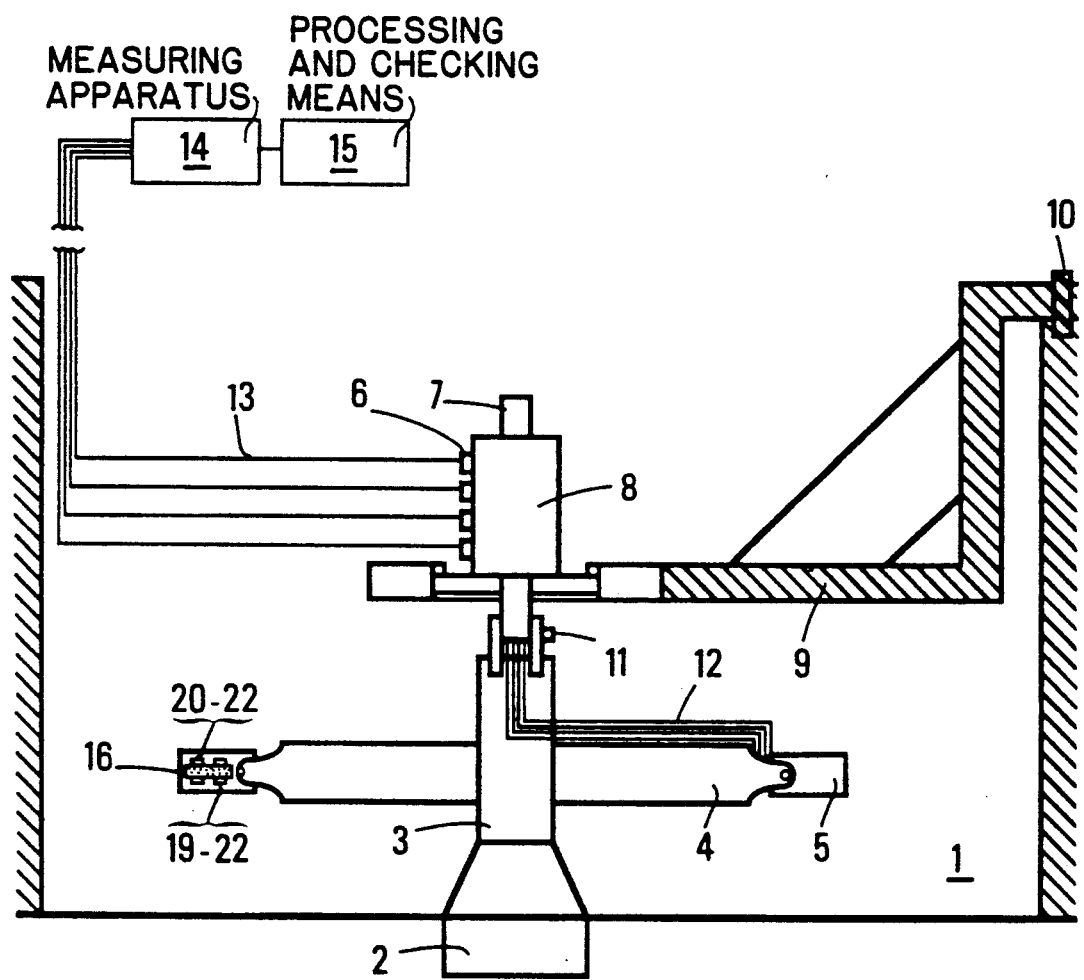
FIG. 2 is a diagrammatic, sectional view of the centrifuge equipped with rotary contacts.

FIG. 2 is an overall view of the apparatus. The cross-section shows the centrifuge (1), which may be of a conventional type or not, e.g. the Cool Spin model distributed by MSE. This centrifuge comprises a motor, which guides a shaft (3). The shaft is fixed to a rotor (4), which e.g. has four arms to which are fitted buckets or cups (5) in which the samples (16) are inserted for centrifuging. An electric rotary contact system (6), e.g. of type T13 distributed by Air Precision is fixed to the rotary shaft of the centrifuge. The contacts are fitted in such a way that the shaft of the contact (7) rotates with the centrifuge shaft, the drum (8) remaining fixed by an arm (9) fitted to the rotary contact system and fitted or not to the exterior (10) of the centrifuge.

The fixing of the rotary electric contacts (11) is carried out in such a way that the wires (12), which are connected to the emitters-receivers, can be fitted with minimum overall dimensions to any randum cup or cups (5).

The transmission of the electric emission and reception signals by the rotary contact system takes place via wires (13) connected to existing terminals on the drum of the electric contact. The wires are connected to measuring apparatuses (14), which are in turn connected to the processing and checking means (15).

The mechanical wave sources are e.g. sound transducers (FIG. 3 (22)), which can be parallelepipedic piezoelectric ceramics, distributed e.g. by Quartz et Silice with the reference P4-68. These ceramics can be constituted by lead titanium zirconate Pb $Ti_{(1-x)}ZR_x O_3$ with x close to 0.5. The same emitter types (19,22) can e.g. be used as mechanical wave receivers (20,22).

Figure 4:
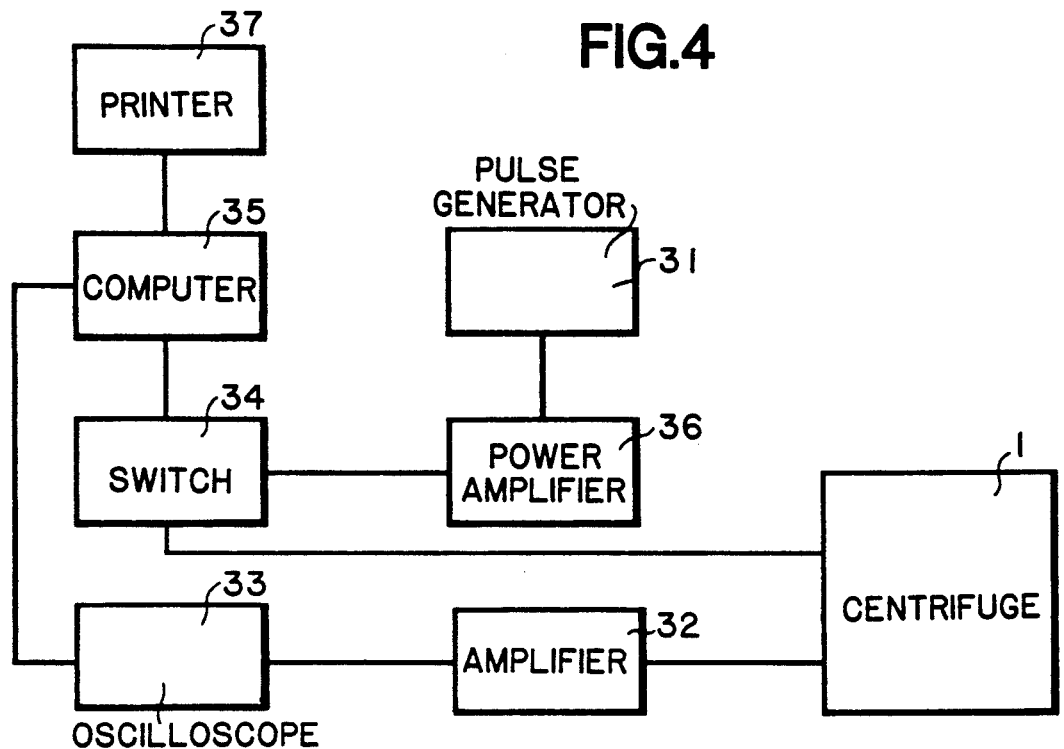
FIG. 4 is a diagram of the different apparatuses and their relative connections to the checking and processing means of the apparatus according to the invention.

The transducers transform the electrical signals into mechanical vibrations. The electric signals are supplied to transducers by a pulse generator (FIG. 4 (31)), such as the Philips PS 51 generator. Due to the two thin metal films covering the opposite faces of the transducer, the electric pulse produces a mechanical wave of the same frequency, which can but need not be the resonant frequency of the transducers. Preferably, it is possible to use sound waves with a wavelength (e.g. 5 to 8 mm) above the characteristic sizes of the studied system, size of the pores of a porous medium, size of the particles of a suspension, in order to limit diffusion phenomena of the mechanical signal in the system. This at least partly attenuated transmitted mechanical signal is transformed into an electric signal by a receiver, which can be the actual emitter, on working with a system in reflection, or can differ therefrom when working with an emitter-receiver pair system. This collected signal is optionally amplified by means of an amplifier (32), e.g. Ultrasonic Preamp distributed by Panametrics.

The emitted and transmitted signals are displayed on the screen of an oscilloscope (33), which can e.g. by an Intelligent Oscilloscope System 5110 distributed by Gould. The opening and closing of the electric circuits connecting the measuring apparatuses to the transducers are ensured by a switch (34), which can be a Kettley 705 scanner. All the instrumentation can be controlled by a computer (35), e.g. a HP 86 or HP Vectors QS 16 s distributed by Hewlett Packard. The emission signal can also be amplified by means of a power amplifier (36), which can be a 2100 L RF Power Amplifier distributed by EIN USA.

The results can be displayed by a printer or plotter (37), a computer console or a video equipment.

Figure 3A:
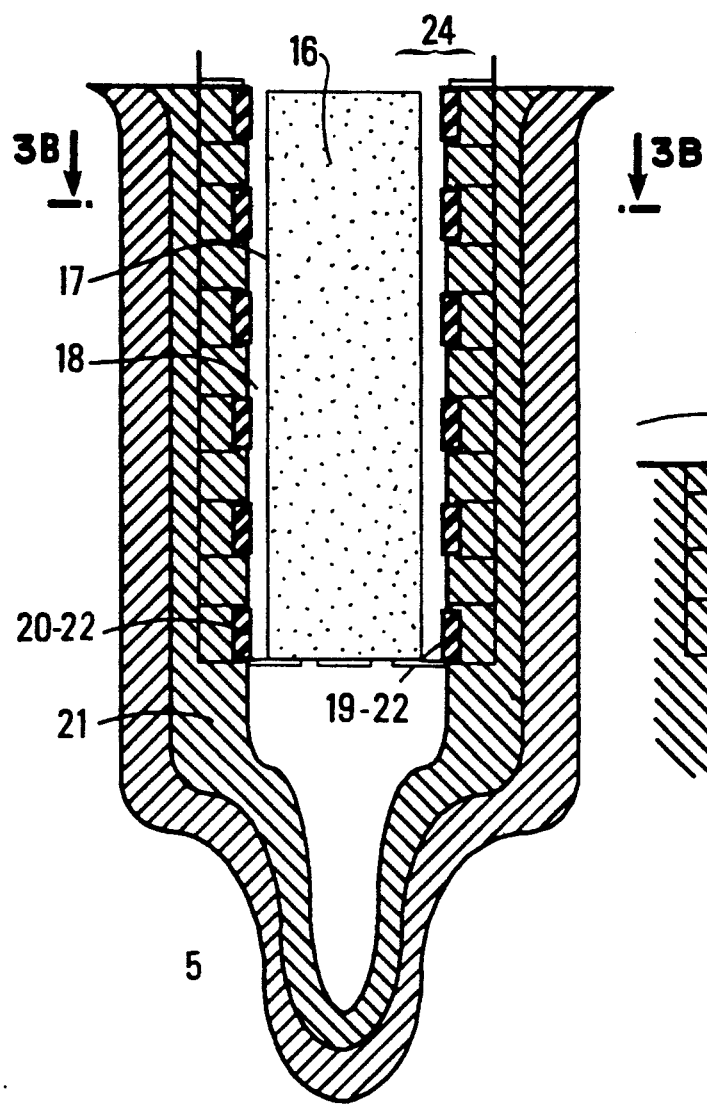
FIGS. 3A, B, and C show a detailed, sectional view of a centrifuge bucket or cup containing the emission-reception system for the mechanical signals and the centrifuged medium.
Figure 3C:
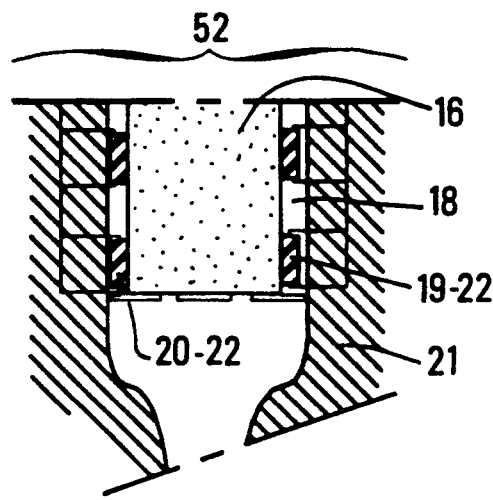

FIGS. 3 show in detailed manner examples of the installation of the buckets or cups used for centrifugal measurements. The sample holder cups are generally cylinders (5), which can be of a metallic nature and internally arranged so as to be able to carry all the transducers. It is possible to fit the transducers (19,20,22) to the actual cups (FIG. 3a). The transducers can also be directly fixed to the sample (FIG. 3c), or between the cup and the sample. The preferably cylindrical sample can be coated with an impermeable sheath (e.g. Teflon) in order to avoid lateral circulations. It can be immersed in a fluid (18), which may be contained in the cup (5).

Figure 3B:
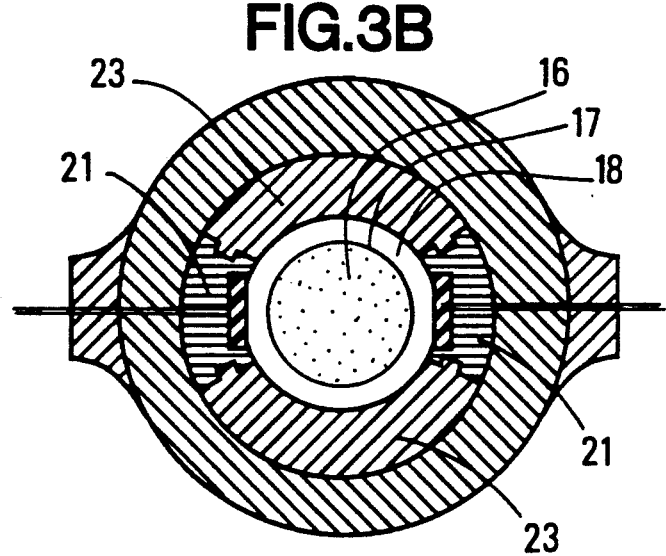

According to FIG. 3B, which is a section along axis 1B of FIG. 3A, the inner wall of the sample holder cup can be coated with a material, which can be a plastics material, in which there is at least one mobile or non-mobile part (21) containing the transducers (22) and a fixed or non-fixed part (23). The mobile part (21) is generally such that several transducers, whose number is only limited by the dimensions of the transducers and the samples, is in contact with the region carrying out the mechanical coupling of the waves (24), namely, but not necessarily, a liquid film (18) around the studied system.

Figure 5:
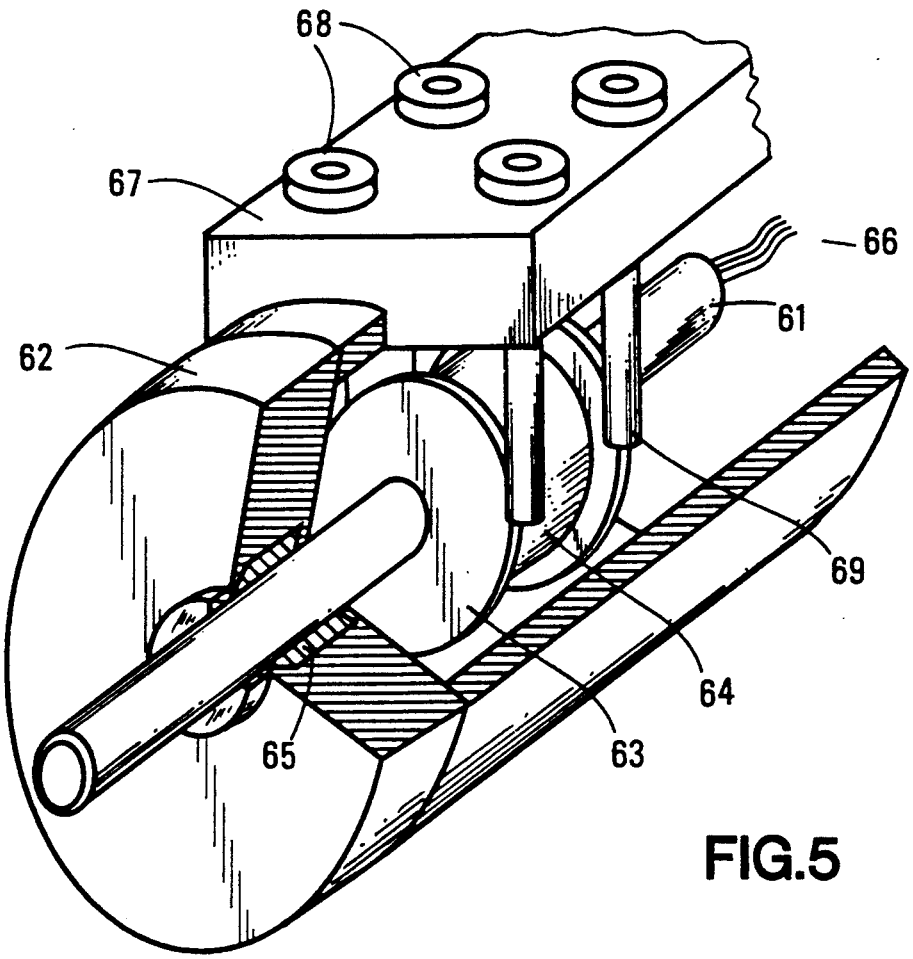
FIG. 5 is a perspective view of a rotary contact system mounted on the shaft of the centrifuge rotor.

The rotary contacts (63, FIG. 5) are constituted by two coaxial cylinders, the main internal spindle (61) and the outer cylinder (62). The spindle is formed by collector rings and resistant rings (64) (the same number as there are contacts) arranged in series along the spindle. Both the spindle and the outer cylinder can rotate by ball bearings (65), while the spindle can be hollow to permit the passage of wires (66). To the outer cylinder is attached a terminal block (67) with the same number of terminals (68) as there are contacts, each contact being connected to a cilium (69), which bears on a collector ring thus forming the contact. The presently available version of the system for transmitting the signals to the checking and processing means and to the centrifuge can function up to a rotation speed of 3500 r.p.m.

The mechanical signals received at the receivers are compared with the emitted signals to e.g. obtain the longitudinal propagation velocity of the fastest mechanical signals between the emitter and the receiver. This comparison is obtained from that of the corresponding electric signals, e.g. displayed on an oscilloscope, as stated hereinbefore.

When measuring the saturations of fluids in a porous medium, the propagation velocities (or propagation times or attenuations) are then transformed into fluid saturations. This transformation uses a calibration, which can be carried out in different ways.

CALIBRATION

When the propagation velocities are measured, an example of a calibration method is described by Bacri and Salin (Bacri J. C. and Salin D., 1986: Sound velocity of a sandstone saturated with oil and brine at different concentrations, Geophysical Research Letters V. 13, 4, pp. 326–328). Before centrifuging, the velocity of sound propagation is measured for different saturations in a given porous medium. The velocity-saturation correspondence is directly deduced from it. This dependence is more particularly dependent on the way in which the fluids are placed in the medium (e.g. injection of wetting or non-wetting fluid). Thus, in this case use is made of the calibration corresponding to the centrifuging to be performed.

As this direct method is relatively long, another calibration can be carried out. The same authors revealed that in the case of a draining, the relationship between the velocity and the saturation can be obtained on the basis of the theory of Biot and Gassmann (Biot M. A., 1956: Theorie of propagation of elastic waves in a fluid saturated porous solid. J. Acous. Soc. Am., 28, 168–191; Gassman F., 1951: Elastic waves through a packing of spheres. Geophys., 16, 673–685).

The mixture of the two fluids in the porous medium is then considered as an equivalent fluid of density P fluid $= S_1 P_1 + S_2 P_2$ and modulus of elasticity $K_{fluid} = 1/(S_1/K_1 + S_2/K_2)$, $S_1 + S_2 = 1$.

According to the theory, the velocity of the fastest longitudinal waves is then $$V = \sqrt{K_{effective}/P_{effective}} \text{ with } 1/\kappa_{effective} = \phi/\kappa_{fluid} + (1-\phi)/\kappa_{solid}$$

$$P_{effective} = a\, P_{fluid} \frac{(1-\phi)p_{solid} + (1-a^{-1})\phi\, p_{fluid}}{\phi(1-\phi)p_{solid} + (a-2\phi+\phi^2)\, p_{fluid}}$$

$K_{effective}$ and $P_{effective}$ are the effective density and compressibility of the medium, is the twist, $1-\phi$ the volume proportion of the solid or the particle concentration in the case of a suspension. As these parameters are the only quantities to be measured in this case, the calibration can be rapidly obtained.

Other calibration methods can also be used. The general principle can be on the one hand to measure the distribution of the fluids in the system to be centrifuged on the basis of conventional procedures (gammagraphy, X-rays, volume or mass balances), or not and on the other hand measure the propagation characteristics of the mechanical signal (transverse/longitudinal velocities, attenuation, etc).

Reconstruction of Profiles or Images with 2 or 3 Dimensions

The reconstruction of a profile and images of concentrations in the centrifuged system is essentially dependent on the number and arrangement of the emitters and receivers around the medium.

In the case of a linear arrangement along the axis of an arm of the centrifuge (FIG. 1), the mean values of the attenuation and transmit time or the velocity of the mechanical signals are obtained at different points of the axis. A continuous profile of these values can then be reconstructed, by interpolation or adjustment by polynomial or exponential functions, e.g. as shown in FIG. 1A, which shows the fluid saturation as a function of the distance along the centrifuge arm axis.

Figure 6A:
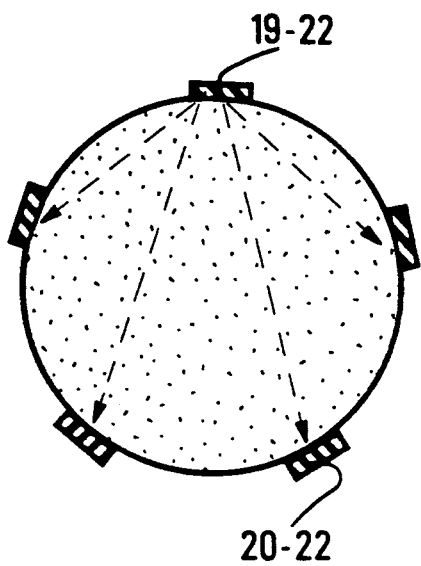
FIGS. 6A, 6B, 6C and 6D examples of the arrangement of sound transducers in the plane of a given section (a) for the multiple acquisition (b) of measurements of velocities, times of flight or attenuation of mechanical signals, with a view to the reconstruction of these quantities throughout the section.
Figure 6B:
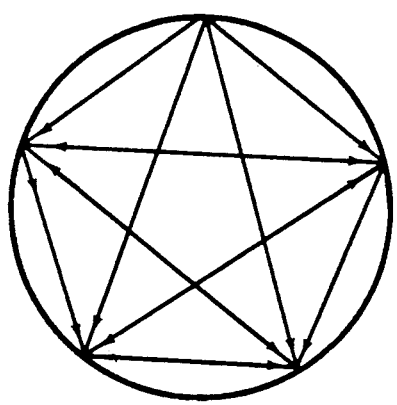
Figure 6C:
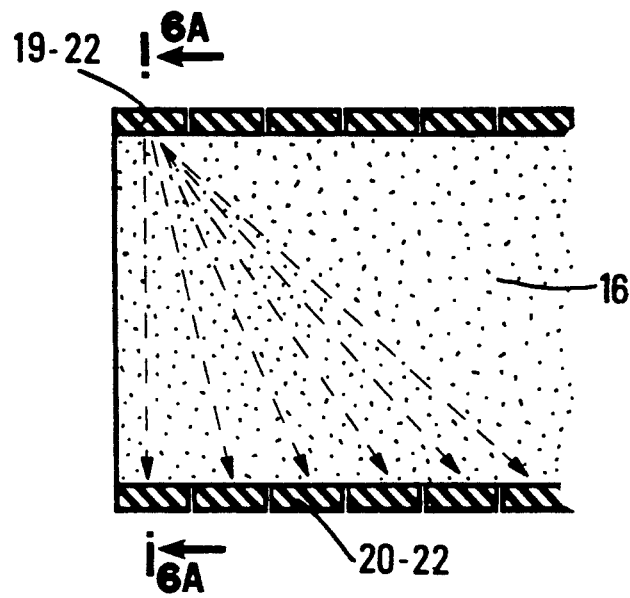
Figure 6D:
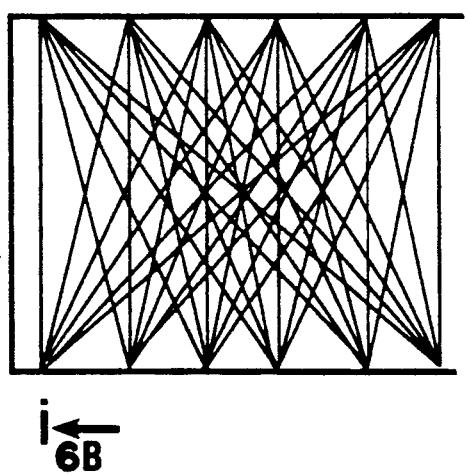

Two-dimensional images could be produced on longitudinal, transverse or similar sections. For this purpose it is necessary to acquire an adequate number of measurements in a sufficiently short time on a given centrifuging system. For example, FIGS. 6C and 6A (sectional view along axis AA) show transverse and longitudinal sections of systems equipped with transducers (22), used as an emitter/receiver. The emission to the transducer 1 is received in 2,3,4,5, ... n, and the emission in 2 is received in 3,4,5,6, ... n,1, and so on. Thus, there are multiple measurements on the different parts of the section (FIGS. 6D and 6B—sectional view along axis BB) and on the basis of these an image can be reconstituted, e.g. using ultrasonic tomography, X-rays or nuclear magnetic resonance (Herman G. T., 1980: Image reconstruction from projections, the fundamentals of computerized tomography. Acad. Press. New York).

It is also possible to reconstitute 3-dimensional images, e.g. on the basis of multiple sections reconstituted at different parts of the system, or directly from sparse measurements in the system (Gordon R. and Herman G. T., 1974: Three-dimensional reconstruction from projections: a review of algorithms. IN, International Review of Cytology, V 38, Bourne and Danielli eds., 111-151).

These reconstructions can also be automated on the computer and used for calculating mean values, on the complete system, of the concentrations of the constituents. These calculated mean values could also be compared with mean values directly measurable during centrifuging at the windows of the buckets or cups. In the case of disagreement a calibration correction method can be used.

The present method can be used for calculating the capillary pressure and relative permeabilities of fluids in a porous medium. In the case where the method is applied to the measurement of reconstitution of profiles along the axis of an arm of the centrifuge, saturations of two fluids 1 and 2 in a porous centrifuged medium, the capillary pressure or relative permeabilities of these fluids can be calculated. The case of an injection of a non-wetting fluid 1 into a porous medium saturated with a fluid 2 is given in an exemplified manner here.

In this case and in accordance with the conventional procedure, the porous medium is centrifuged at a substantially constant rotation speed V until equilibrium is reached, i.e. until there is no longer any displacement of fluids towards the outside of the medium (checking taking place through the window at the end of the bucket), i.e. r is the distance to the axis of the centrifuge and $r_1$ and $r_2$ the densities of the two fluids.

Figure 7A:
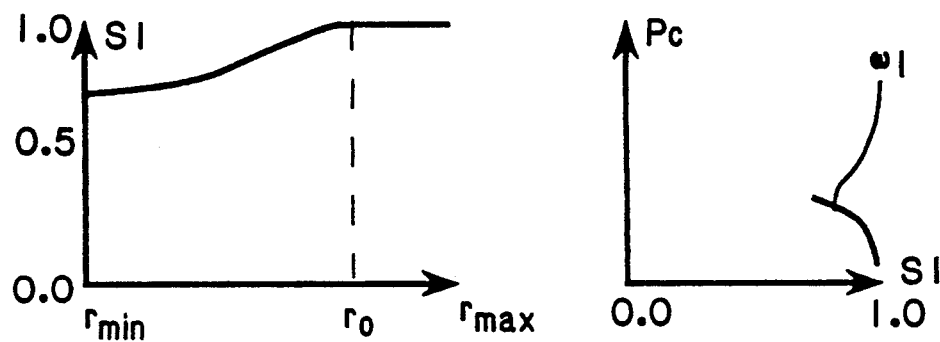
FIGS. 7A, 7B and 7C illustrate an example of a method for obtaining the relationship between the capillary pressure Pc and the fluid saturation S1 and optionally the centrifugal speed.

For a given, sufficiently low velocity V, the saturation $S_2$ in fluid 2 and consequently the capillary pressure remain zero in a part or at the end of the porous medium. The Hassler and Brunner (1945) approach then applies and at a distance r, the capillary pressure is written $Pc_{(r)} = \frac{1}{2}(r_1 - r_2)V^2(r_0^2 - r^2)$; $r_0$ designating the value of r at which the saturation is fluid 2 becomes zero (FIG. 7a).

This value of $r_{max}$ and the complete saturation profile $S_{1(r)}$ in fluid 1 are supplied by the method according to the invention. Thus, knowing $Pc_{(r)}$ and $S_{1(r)}$, it is possible to immediately reconstruct $Pc_{(S1)}$ for $S_1$ in the interval $I_1$:

$$(S_{1(rmin)}, 1).$$

Figure 7B:
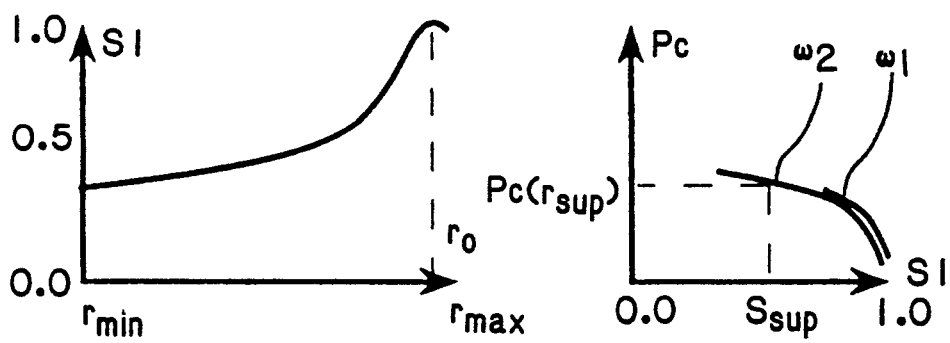

The rotation speed can then be increased in accordance with a random or predetermined number of ranges. This has the effect of forcing $r_0$ towards $r_{max}$ and to reduce $S_{1(rmin)}$. If $r_0$ remains equal to or below $r_{max}$ (Hassler and Brunner condition), we thus obtain $Pc_{S1}$ over a range of values for $S_1$ covering the preceding interval $I_1$. If the porous medium is homogeneous and if the capillary pressure law is not dependent on the rotation speed V or the way in which it is reached, the curve $Pc_{(S1)}$ obtained in this way contains the previous one (FIG. 7b).

Figure 7C:
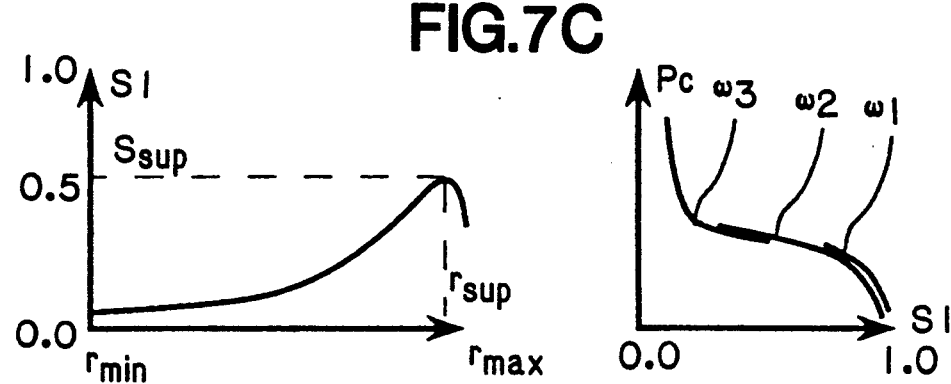

In this connection, use can be made of the invention for estimating the homogeneity of a medium or the possible dependence of the capillary pressure law as a function of the rotation speed and the way in which it is reached. If there is no longer a zone where the saturation in fluid 2 is zero, $S_1$ varies in the interval $I_2 = (S_{1(rmin)} S_{sup})$, it is e.g. proposed to make use of the already determined part of the curve $Pc_{S1}$. From the measured profile is deduced the radius $r_{sup}$ at which the value $S_{sup}$ is reached. From the curve $Pc_{S1}$ is deduced the corresponding capillary pressure, which makes it possible to write for r below $r_{sup}$ $Pc_{(r)} = \frac{1}{2}(r_1 31 r_2) V^2 (r_{sup}^2 - r^2) + Pc_{(rsup)}$. This makes it possible to obtain $Pc_{(S1)}$ on the interval $I_2$ and therefore to complete the already determined curve to the extent that $$S_{1(rmin)}$$

is smaller for the interval $I_2$ than for $I_1$ (FIG. 7c). Thus, the rotation speed can be increased within the limits of the equipment to cover the greatest part possible of the interval ($S_1$ irreducible, 1).

The determination of the optimum rotation speeds, the choice of the speed ranges and the identification of $Pc_{(S1)}$ can be controlled by the computer.

The relative permeabilities $k_i$ can be obtained by different methods and in particular on the basis of saturation profiles at different times. For example, a relation can be obtained between the two relative permeabilities in the form:

$m_1$, and $m_2$ being the viscosities of the fluids 1 and 2

$$\frac{m_1}{k_1} \int_r^{r_{min}} \phi \frac{dS_1}{dt} dr + \frac{m_2}{k_2} \int_r^{r_0} \phi \frac{dS_1}{dt} dr =$$

$$k\left(\frac{dPc}{dr} + (r_1 - r_2)V^2 r\right)$$

At a centrifuging time t, the relation $Pc_{S1}$ and the profile $S_1(r,t)$ supply $Pc(r,t)$ and then $dPc/dr$. The profile $S_1(r,t)$ supplies $r_0$ and the profile $S_1(r,t+dt)$ measured at $t+dt$ makes it possible to obtain $dS_1/dt$. As the other quantities are known, the relation is written $$A_{(r,t)} \frac{1}{k_1(r,t)} + B_{(r,t)} \frac{m_1}{k_2(r,t)} = C_{(r,t)},$$

which is transformed into $$A_{(S1)} \frac{1}{k_1(S_1)} + B_{(S1)} \frac{1}{k_2(S_1)} = C_{(S1)}$$

using the profile $S_1(r,t)$. If the medium is homogeneous and if the relative permeabilities are not dependent on the rotation speed V or the way in which it is reached, this relation is effectively not dependent on the time (or V). As for the capillary pressure, it is here again possible to test these hypotheses or measure a possible dependence.

This relation makes is possible to obtain the relative permeabilities if another relation is available. The ratio of the relative permeabilities can be obtained by the Welge method (Welge H., 1952: A simplified method for computing oil recovery by gas or water drive. Trans AIME, V. 195, 91).

In the absence of a complementary relation, other methods can be used. For example, numerical simulations of the centrifuge can be used for obtaining curves $k_{1(S_1)}$ and $k_{2(S_1)}$, which lead to a better simulation. The method according to the invention supplies a reliable capillary pressure curve for this simulation and supplies a large number of saturation measurements or profiles during centrifuging which can be reproduced by the simulation, so that the curves $k_{1(S_1)}$ and $k_{2(S_1)}$ are given greater accuracy.

We claim:

1. A process for the measurement of the distribution of the concentrations of constituents of a porous solid medium containing at least one fluid, comprising centrifuging under appropriate conditions, of the medium in a centrifuge comprising a centrifuge arm and characterized by the following stages:
   (a) during centrifuging, a mechanical signal is emitted in an adequate frequency and intensity range from at least one emission point in contact with or in the immediate vicinity of the centrifuged medium,
   (b) a corresponding transmitted signal is received by at least one reception point in contact with or in the immediate vicinity of the centrifuged medium after the mechanical signal has traversed a part of said medium lying between said at least one emission point and said at least one reception point,
   (c) for each pair of emission and reception points, a measurement is performed of at least one propagation characteristic of the mechanical signal, and
   (d) the distribution of the concentrations of the constituents in the porous solid medium is determined by appropriate processing means from said measurements of the propagation characteristics of the signal.

2. A process according to claim 1, wherein, during stage (a), the signal is emitted by a plurality of emission points either simultaneously or successively.

3. A process according to claim 1, wherein, during stage (b), at least one emission point is used at least once as the reception point.

4. A process according to claim 1, wherein stages (a), (b), (c), and (d) are repeated at different times to obtain said distribution of the concentrations of the constituents of the medium at these different times.

5. A process according to claim 1, wherein a plurality of emission points and a plurality of reception points are located in a plane of a section of the centrifuged medium and wherein the distribution of the concentrations of the constituents of the medium in this plane is determined.

6. A process according to claim 1, wherein a plurality of emission points and a plurality of reception points are located in a direction along which is determined the distribution of the concentrations of the constituents.

7. A process according to claim 1, wherein the mechanical signal has a frequency between 100 and 2000 kHz.

8. A process according to claim 7, wherein the mechanical signal is a sound wave of 250 to 500 kHz.

9. A process according to claim 1, wherein the medium is a porous medium containing two fluids.

10. A process according to claim 1, wherein said at least one fluid comprises a suspension of particles or an emulsion.

11. Process according to claim 6, wherein said direction of the emission and reception points along which the determination of said distribution is made is that of an axis of the centrifuge arm.

12. A process according to claim 1, wherein said at least one propagation characteristic of the mechanical signal is the propagation velocity in the medium between the emission point and the reception point of said signal.

13. Apparatus for measuring the distribution of concentrations of constituents of a medium, comprising in combination:
   a centrifuge having a centrifuge arm and a predetermined number of sample holders containing the said medium, said centrifuge being able to operate at a plurality of rotation speeds;
   a plurality of emission sources for emitting mechanical signals, said emission sources being able to provide energy of a sufficient intensity and frequency range within or in the immediate vicinity of at least one of said sample holders, said emission sources being positioned at a spaced location along a radial direction of the centrifuge arm;
   at least one reception means for receiving transmitted mechanical signals having traversed the medium, said reception means being contained in or in the immediate vicinity of said at least one sample holder;
   rotary contact means suitable for transmission, during rotation, of electric signals for producing said emitted mechanical signals, said rotary contact means further being suitable for transmission, during rotation, of electric signals produced by said reception means;
   means for measuring a propagation characteristic of said transmitted mechanical signals, said means for measuring being connected to said emission sources and to said reception means via said rotary contact means;
   processing and checking means for determining a measurement of said distribution of concentrations, said processing and checking means being connected to said measuring means and to said centrifuge.

14. Apparatus according to claim 13, wherein at least one of said plurality of signal emission sources is a sound transducer able to generate mechanical waves in the frequency range 100 to 2000 kHz.

15. Apparatus according to claim 13, wherein the emission sources and the reception means of the signals are such that at least one of the emission sources is used as a reception means of the mechanical signal.

16. An apparatus according to claim 13, wherein each of said plurality of emission sources is able to generate a single frequency wave between 250 and 500 KHz.

17. A process for measurement of a distribution of concentrations of constituents of a medium containing at least one fluid, comprising centrifuging under appropriate conditions, of the medium in a centrifuge comprising a centrifuge arm and characterized by the following stages:
   (a) during centrifuging, a mechanical signal is emitted at an adequate frequency and intensity range from a plurality of emission points at spaced locations along a length of travel traversing a plurality of constituents within the medium and in contact with or in the immediate vicinity of the centrifuged medium,
   (b) a corresponding transmitted signal is received by at least one reception point in contact with or in the immediate vicinity of the centrifuged medium after the mechanical signal has traversed a part of said medium lying between said at least one emission point and said at least one reception point,
(c) for each pair of emission and reception points, a measurement is performed of at least one propagation characteristic of the mechanical signal, and
(d) the distribution of the concentrations of the constituents in the medium is determined by appropriate processing means from said measurements of the propagation characteristics of the signal.

18. A process according to claim 17, wherein said medium is a porous solid medium.

* * * * *